United States Patent
Ahn et al.

(10) Patent No.: US 12,011,447 B2
(45) Date of Patent: Jun. 18, 2024

(54) PHARMACEUTICAL COMPOSITION FOR TREATING THYROID CANCER COMPRISING TYROSINE KINASE ACTIVITY INHIBITOR AS ACTIVE INGREDIENT

(71) Applicant: Kyungpook National University Industry-Academic Cooperation Foundation, Daegu (KR)

(72) Inventors: Byeong Cheol Ahn, Daegu (KR); Ji Min Oh, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 197 days.

(21) Appl. No.: 17/886,099

(22) Filed: Aug. 11, 2022

(65) Prior Publication Data

US 2022/0378796 A1    Dec. 1, 2022

Related U.S. Application Data

(63) Continuation of application No. 16/757,486, filed as application No. PCT/KR2018/012385 on Oct. 19, 2018, now abandoned.

(30) Foreign Application Priority Data

Oct. 20, 2017   (KR) ........................ 10-2017-0136722

(51) Int. Cl.
*A61K 31/519*     (2006.01)
*A61P 35/04*      (2006.01)

(52) U.S. Cl.
CPC ............ *A61K 31/519* (2013.01); *A61P 35/04* (2018.01)

(58) Field of Classification Search
CPC .............................. A61K 31/519; A61P 35/00
See application file for complete search history.

(56) References Cited

U.S. PATENT DOCUMENTS

2010/0063047 A1    3/2010   Borchardt
2012/0136014 A1    5/2012   Chen et al.

FOREIGN PATENT DOCUMENTS

WO    2017/031176    2/2017

OTHER PUBLICATIONS

International Search Report issuing in counterpart PCT Application No. PCT/KR2018/012385, dated Jan. 25, 2019.
Oh, Ji Min. Screening of sodium/iodide symporter (NIS) enhancer with high-throughput drug screening platform using dual reporter gene molecular imaging system. Thesis for the Degree of Master of Science. The Graduate School, Kyungpook National University. Jun. 2017.
Gangjee. A. et al. 6-Substituted 2,4-Diaminopyrido [3,2-d]pyrimidine Analogues of Piritrexim as Inhibitors of Dihydrofolate Reductase from Rat Liver, Pneumocystis carinii, and Toxoplasma gondii and as Antitumor Agents. J. Med. Chem. 1998, 41, 4533-4541.
CAS Registry No. 434915-02-3. Entered STN: Jun. 28, 2002.

*Primary Examiner* — Shobha Kantamneni
(74) *Attorney, Agent, or Firm* — WENDEROTH, LIND & PONACK, L.L.P.

(57) ABSTRACT

A pharmaceutical composition containing a tyrosine kinase activity inhibitor as an active ingredient may increase the expression of sodium iodide symporter in thyroid cancer cells, thereby promoting iodine uptake and killing thyroid cancer cells. Thus, the composition may be useful for the treatment of thyroid cancer.

5 Claims, 16 Drawing Sheets

PHARMACEUTICAL COMPOSITION FOR TREATING THYROID CANCER COMPRISING TYROSINE KINASE ACTIVITY INHIBITOR AS ACTIVE INGREDIENT

TECHNICAL FIELD

The disclosure relates to a pharmaceutical composition for treating thyroid cancer containing a tyrosine kinase activity inhibitor as an active ingredient.

BACKGROUND ART

Thyroid cancer is the most common tumor of the endocrine system, and examples thereof include papillary carcinoma, follicular carcinoma, Hurtle cell neoplasm, anaplastic carcinoma (undifferentiated thyroid cancer), medullary thyroid carcinoma, and the like. Among these, differentiated tumors such as thyroid papillary carcinoma and thyroid follicular carcinoma show a relatively good prognosis, but in the case in which these tumors infiltrated the surrounding tissues or metastasized to other organs, the survival rate of patients with these tumors decreases rapidly. Anaplastic carcinoma is a rare, highly malignant undifferentiated tumor which is characterized by aggressiveness, rapid progression, a poor prognosis, and high mortality. Unlike differentiated thyroid cancer, anaplastic carcinoma does not exhibit the characteristics of thyroid follicular cells, such as iodine uptake and thyroglobulin synthesis, and is resistant to radioactive iodine (RAI) therapy due to the reduced iodine uptake thereof.

Sodium iodide symporter (NIS) is an intrinsic transmembrane glycoprotein, and co-transports two sodium cations ($Na^{2+}$) and one iodine anion ($I^-$) across the basolateral membrane of thyroid follicular cells. Anaplastic carcinoma shows the worst prognosis among thyroid carcinomas due to suppressed expression of the sodium iodide symporter therein and the reduced iodine uptake thereof.

DISCLOSURE

Technical Problem

One object of the present disclosure is to provide a composition for treating or preventing thyroid cancer and an anticancer adjuvant for thyroid cancer, which contain, as an active ingredient, a compound of the following Formula 1, a salt thereof or a solvate thereof:

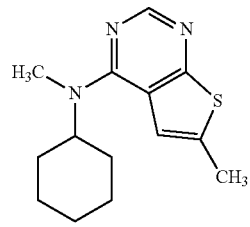

[Formula 1]

Technical Solution

One aspect of the present disclosure is directed to a composition for treating or preventing thyroid cancer containing, as an active ingredient, a compound of the following Formula 1, a salt thereof or a solvate thereof:

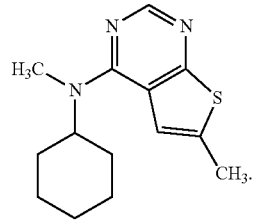

[Formula 1]

According to one embodiment of the present disclosure, the thyroid cancer may be anaplastic thyroid cancer or differentiated thyroid cancer.

According to one embodiment of the present disclosure, the compound of Formula 1 may increase the expression of sodium iodide symporter.

Another aspect of the present disclosure is directed to an anticancer adjuvant for thyroid cancer containing, as an active ingredient, a compound of the following Formula 1, a salt thereof or a solvate thereof:

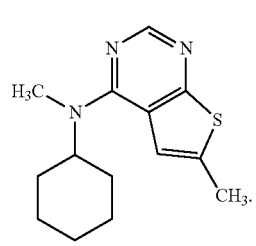

[Formula 1]

According to one embodiment of the present disclosure, the compound of Formula 1 may increase the expression of sodium iodide symporter.

Advantageous Effects

The use of the composition according to one embodiment of the present disclosure may increase the expression of sodium iodide symporter in thyroid cancer cells, thereby promoting iodine uptake and killing thyroid cancer cells. Thus, the composition may be useful for the treatment of thyroid cancer.

BEST MODE

Figure 1:
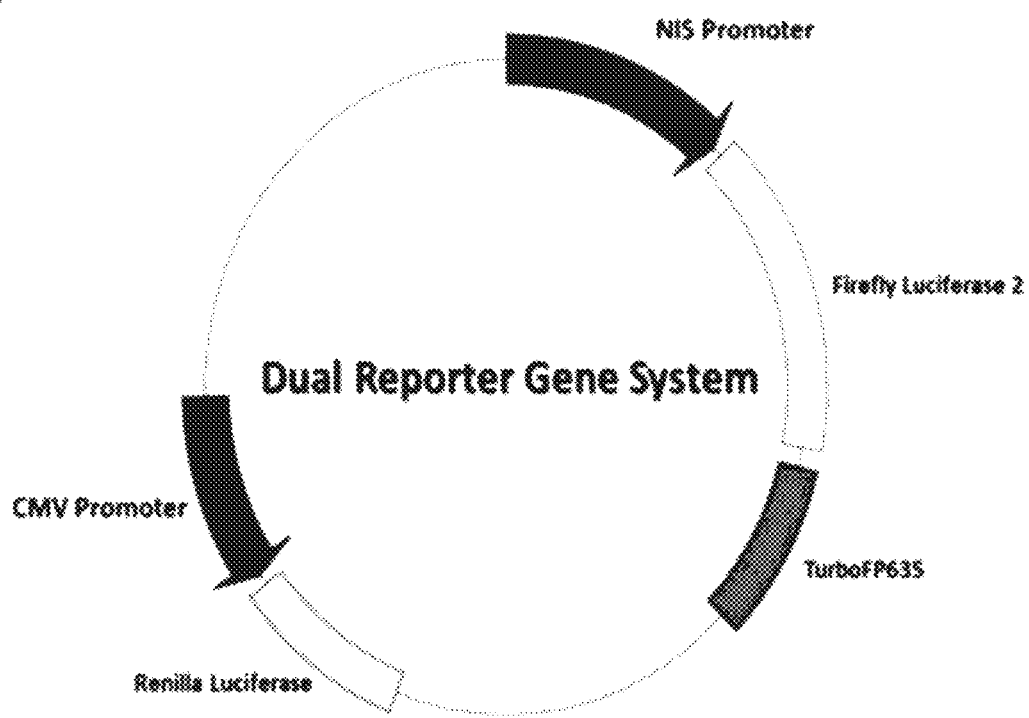
FIG. 1 is a view showing the structure of a pNIS-FL2-TurboFP635-pCMV-Rluc vector containing a dual promoter system.

One aspect of the present disclosure is directed to a composition for treating or preventing thyroid cancer containing, as an active ingredient, a compound of the following Formula 1, a salt thereof or a solvate thereof:

[Formula 1]

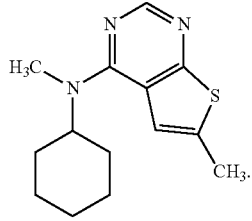

According to one embodiment of the present disclosure, the compound of Formula 1 may be obtained by extraction and separation from natural products or produced by a conventional organic synthesis method, but is not limited thereto.

According to one embodiment of the present disclosure, the thyroid cancer may be undifferentiated thyroid cancer (anaplastic thyroid cancer) or differentiated thyroid cancer, but is not limited thereto. Unlike differentiated thyroid cancer, undifferentiated thyroid cancer has suppressed expression of the sodium iodine symptor and reduced iodine uptake.

According to one embodiment of the present disclosure, the compound of Formula 1 may increase the expression of sodium iodide symporter in thyroid cancer cells, thereby promoting the uptake of radioactive iodine and killing thyroid cancer cells. The compound of Formula 1 may also decrease colony-forming ability in cancer cell.

The pharmaceutical composition of the present disclosure may further contain pharmaceutically acceptable additives. As the pharmaceutically acceptable additives, there may be used starch, gelatinized starch, microcrystalline cellulose, lactose, povidone, colloidal silicon dioxide, calcium hydrogen phosphate, lactose, mannitol, maltose, gum Arabic, pregelatinized starch, corn starch, powdered cellulose, hydroxypropyl cellulose, Opadry, sodium starch glycolate, carnauba wax, synthetic aluminum silicate, stearic acid, magnesium stearate, aluminum stearate, calcium stearate, white sugar, dextrose, sorbitol, and talc.

The composition of the present disclosure may be administered in various oral and parenteral formulations for actual clinical administration. For formulation, preparation may be performed by using a normally used diluents or excipients such as a filler, an extender, a binder, a wetting agent, a disintegrating agent, and a surfactant. Examples of solid formulations for oral administration include a tablet, a pill, power, a granule, a capsule, etc. The solid formulations may be prepared by mixing a herbal composition of the present invention having an increased content of oil-soluble polyphenol with at least one excipient such as starch, calcium carbonate, sucrose, lactose or gelatin. In addition to simple excipients, lubricants such as magnesium stearate or talc may also be used.

The composition of the present disclosure can be administered orally or parenterally in accordance with the desired method. When the composition is administered parenterally, the administration method is preferably selected from intraperitoneal injection, intrarectal injection, subcutaneous injection, intravenous injection, intramuscular injection and intrathoracic injection. The dose range of the composition varies depending on the patient's body weight, age, sex, health condition, diet, time of administration, administration method, excretion rate, and disease severity.

The composition according to the present disclosure may be administered in a pharmaceutically effective amount. In the present disclosure, "pharmaceutically effective amount" refers to an amount sufficient to treat diseases, at a reasonable benefit/risk ratio applicable to any medical treatment. The effective dosage level of the composition may be determined depending on factors, including the type and the severity of the disease, the activity of the drug, the patient's sensitivity to the drug, the time of administration, the route of administration, the excretion rate, the duration of treatment, and drugs used in combination with the composition, and other factors well known in the medical field. The composition of the present disclosure may be administered individually or in combination with other therapeutic agents, and may be administered sequentially or simultaneously with conventional therapeutic agents. The composition may be administered in a single or multiple dosage form. It is important to administer the composition in the minimum amount that can exhibit the maximum effect without causing side effects, in view of all the above-described factors, and this amount can be easily determined by a person skilled in the art.

Specifically, the effective dosage of the composition according to the present disclosure may vary depending on the patient's age, sex and body weight. In general, the composition may be administered daily or every other day or administered 1 to 3 times a day, at a dosage of 1 mg to 200 mg per kg of body weight, preferably 10 mg to 200 mg per kg of body weight. However, the dosage is not intended to limit the scope of the present disclosure in any way, because it may vary depending on the route of administration, the severity of the disease, the patient's sex, body weight, and age, etc.

Another aspect of the present disclosure is directed to an anticancer adjuvant for thyroid cancer containing, as an active ingredient, a compound of the following Formula 1, a salt thereof or a solvate thereof:

[Formula 1]

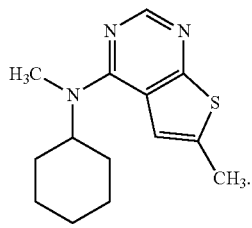

As used herein, the term 'anticancer adjuvant' refers to an agent capable of improving, enhancing or increasing the anticancer effect of an anticancer drug. For example, when an agent that exhibits anticancer activity in a concentration-dependent manner is used together with an anticancer drug at a level that does not exhibit any anticancer activity by itself, the agent may be used as an anticancer adjuvant capable of improving, enhancing or increasing the anticancer effect of the anticancer drug.

According to one embodiment of the present disclosure, since the compound of Formula 1 may promote the uptake of radioactive iodine by increasing the expression of sodium iodide symporter, it may be used as an anticancer adjuvant for the treatment of thyroid cancer, and may be co-administered with $^{131}I$ in the treatment of thyroid cancer.

The anticancer adjuvant may be administered through any normal route, as long as it may reach a target tissue. The anticancer adjuvant of the present disclosure may be administered intraperitoneally, intravenously, intramuscularly, subcutaneously, intradermally or orally, depending on the intended use thereof, but is not limited thereto. In addition, the anticancer adjuvant may be administered using any device capable of delivering the active ingredient to a target cell.

Furthermore, the anticancer adjuvant may be administered alone before or after administration of an anticancer drug, or may be co-administered as an adjuvant for cancer therapy with an anticancer drug. When the anticancer adjuvant of the present disclosure is co-administered with an anticancer drug, it may be co-administered with the anticancer drug at a suitable ratio depending on the patient's condition, the dosage of the anticancer drug, and the administration duration of the anticancer drug. Specifically, the anticancer adjuvant may be administered in an amount equal to 0.01 to 10 times the total weight of the anticancer drug.

Mode for Invention

Hereafter, one or more embodiments will be described in more detail with reference to examples. However, these examples are merely to illustrate one or more embodiments, and the scope of the present disclosure is not limited to these examples.

Experimental Methods

1. Cell Culture 8505C cells, which are a human anaplastic thyroid cancer (hereinafter referred to as ATC) cell line, were cultured with RPMI-1640 medium (Hyclone) containing 10% fetal bovine serum (FBS; Gibco) and 1% penicillin-streptomycin (Hyclone) in a humidified incubator at 37° C. under 5% $CO_2$.

2. Construction of pNIS-FL2-TurboFP635-pCMV-Rluc Recombinant Vector

A pNIS-FL2-TurboFP635-pCMV-Rluc recombinant vector expressing reporter genes driven by dual promoters was constructed by Cosmo Genetech, Ltd. (Republic of Korea) using a pNIS-FL2-TurboFP635 vector and a pcDNA3.1/Hygro(+) vector. Specifically, in order to screen a substance that increases the activity of NIS promoter, Firefly-luciferase2(F-luc2) and TurboFP635 were included downstream (clockwise) of the NIS promoter. In order count cells, CMV promoter and Renilla-luciferase (R-luc) were included upstream (counterclockwise) of the NIS promoter. The pNIS-FL2-TurboFP635 vector was provided from Dr. Abhijit De (ACTREC, India), and the pcDNA3.1/Hygro(+) vector was purchased from invitrogen (USA).

3. Establishment of Stable Cell Line

The 8505C cell line was transfected with the pNIS-FL2-TurboFP635-pCMV-Rluc recombinant vector using the Fu-GENE HD solution according to the protocols of the manufacturer (Promega). The ratio of the recombinant vector to the Fu-GENE HD solution was 1:4, and the transfected cells were selected using 600 µg/ml of geneticin (AG Scientific). The selected cell line that stably expresses the dual-reporter gene system is referred to herein as '8505C-PNIS-PCMV' cell line.

4. Screening of Substance that Increases Expression of Sodium Iodide Symporter

To examine transcriptional regulation of the NIS (sodium iodide symporter) promoter, the 8505C-PNIS-PCMV cells were treated with a tyrosine kinase inhibitor (hereinafter referred to as TKI) library for 24 hours. Next, D-luciferin (150 µg/ml) was added to the cells, and the activity of NIS promoter was measured by IVIS Lumina III (Perkin-Elmer, Wellesley, Mass., USA). To normalize the NIS promoter activity to cell number, 10 µg/ml of h-coelenterazine was added to the cells, and the activity of R-luc was measured. The activity of F-luc2 was divided by the R-luc activity. The TKI library used in the experiment was obtained from the Korea Chemical Bank (www.chembank.org) in the Korea Research Institute of Chemical Technology (Republic of Korea). Among the TKI candidates, TKI-0266 was selected, purchased from Chemdiv (USA), dissolved in DMSO, and then stored at −80° C.

5. Protein Isolation and Western Blotting

8505C-PNIS-PCMV cells were treated with TKI-0266 and incubated for 24 hours, and then the cell pellet was washed twice with cold phosphate-buffered saline (hereinafter referred to as PBS). An RIPA buffer (Thermo Fisher Scientific, USA) containing a protease/phosphatase cocktail inhibitor kit (Thermo Fisher Scientific) was added to the cell pellet to lyse the cells. The lysed cells were gently vortexed three times at a time interval, and centrifuged at 13000xg at 4° C. to isolate a soluble protein. The isolated protein was quantified using a BCA protein assay kit (Thermo Fisher Scientific).

Membrane protein and cytosolic protein were isolated using Mem-PET™ plus kit (Thermo Fisher scientific) according to the manufacturer's protocols. Briefly, the collected cell pellet was washed with a cell wash solution and centrifuged at 300xg for 5 minutes, and this washing and centrifugation process was repeated two times. After centrifugation, the supernatant was discarded, and a permeabilization buffer was added to the cell pellet, followed by vortexing. Thereafter, the cell pellet was left to stand at 4° C. for 10 minutes with continuous stirring. After centrifugation, the supernatant containing cytosolic protein was collected, and a solubilization buffer was added to the remaining cell pellet which was then left to stand at 4° C. for 10 minutes with continuous stirring. After centrifugation again at 300xg for 5 minutes, the membrane protein was transferred into a fresh tube.

Equal amounts of proteins were separated by 10% SDS-PAGE (sodium dodecyl sulfate-polyacrylamide gel electrophoresis), and then the proteins were transferred to PVDF membranes (Millipore, USA). The PVDF membrane was blocked with 3% BSA (bovine serum albumin) in TBS containing Tween-20 (TBS-T) for 1 hour, and incubated with primary antibodies in 0.5% BSA overnight at 4° C. The next day, the PVDF membrane was incubated with HRP-conjugated secondary antibodies at room temperature for 1 hour, and washed three times with TBS-T. The protein bands were visualized using ECL detection reagent (GE Healthcare Life Sciences, Italy) and the Fusion FX chemiluminescence analyzer system (Vilber lourmat, France).

The primary antibodies used in the experiment were as follows: NIS (Thermo Fisher Scientific; working dilution 1:2500), Phospho-p44/42 MAPK (p-ERK1/2) (Cell Signaling; dilution 1:2500), p44/42 MAPK (Total ERK1/2) (Cell Signaling; dilution 1:2500), Phospho-Akt (Cell Signaling; dilution 1:2500), Akt (Cell Signaling; dilution 1:2500), Thyroglobulin (Santa Cruz Biotechnology; dilution 1:2000), TSHR (Santa Cruz Biotechnology; dilution 1:2000), Thyroperoxidase (Santa Cruz Biotechnology; dilution 1:2000), TTF-1 (Santa Cruz Biotechnology; dilution 1:2000), Pax-8 (Santa Cruz Biotechnology; dilution 1:2000), Luciferase (Promega; dilution 1:5000), Renilla luciferase (Abeam; dilution 1:5000), GAPDH (Santa Cruz Biotechnology; dilution 1:5000) and β-actin (Santa Cruz Biotechnology; dilution 1:5000), HRP-conjugated secondary antibodies used in the experiment were anti-mouse (Cell Signaling) and anti-rabbit (Cell Signaling) antibodies.

6. In vitro $^{125}$I Uptake Assay 8505C cells ($1.25 \times 10^5$) were seeded and incubated in a 24-well plate for 24 hours, and then treated with TKI-0266 and further incubated for 24 hours. Thereafter, the medium was removed, and the cells were washed with bHBSS (Hank's balanced salt solution containing 0.5% BSA). The cells were incubated with 500 µl of bHBSS, 3.7 kBq carrier-free $^{125}$I (Perkin-Elmer), and 10 µmol/L sodium iodide (specific activity of 740 MBq/mmol) at 37° C. for 30 minutes. Thereafter, the cells were washed twice with cold bHBSS and lysed by adding 500 µL of 2% SDS solution thereto. Radioactivity was measured using a Cobra II gamma-counter (Canberra Packard, Canada). The $^{125}$I uptake values were normalized by comparing the amount of total protein determined by BCA protein assay kit.

7. $^{131}$I Clonogenic Assay 8505C cells ($4 \times 10^5$) cells were seeded in a six-well plate, and then treated with TKI-0266 and incubated for 24 hours. Next, the medium was removed, and the cells were washed twice with bHBSS, and then incubated in the presence or absence of 50 µCi/ml $^{131}$I (KIRAMS, Korea) containing 30 µM NaI for 7 hours at 37° C. After incubation, the cells were washed twice with bHBSS, re-seeded in a new six-well plate at a density of 1,000 cells/well, and then incubated for 7 days to induce colony formation. On day 7, the medium was removed and the cells were washed twice with PBS. A fixation buffer containing acetic acid:methanol at a ratio of 1:7 was added to the cells and the plate was left to stand at room temperature for 5 minutes to fix colonies. The fixed colonies were stained with 0.05% crystal violet for 1 hour and immersed in tap water to remove crystal violet. The colonies containing 50 or more cells were counted. Percentage inhibition was calculated as the number of colonies formed in the TKI-0266-treated group relative to the vehicle control.

8. Immunofluorescence Microscopy 8505C cells were seeded in a plate at a density of $2 \times 10^5$ cells and treated with the TKI inhibitor TKI-0266. After 24 hours, the cells were fixed with 4% paraformaldehyde for 30 minutes at room temperature and washed three times with PBS for 10 minutes each wash. Next, the cells were treated with PBS containing 0.7% Triton for 10 minutes at room temperature and quenched with PBS containing 50 mM $NH_4Cl$ for 10 minutes at room temperature. The cells were washed three times with PBS for 5 minutes each wash, and then blocked with 5% BSA-containing PBS and incubated with anti-NIS primary antibody (diluted at 1:50; Abcam, UK) overnight at 4° C. The next day, the cells were washed three times with PBS for 10 minutes each wash and incubated with Alexa-Fluor 488-conjugated secondary antibody (diluted at 1:300; Thermo Fisher Scientific) 1 hour. After 1 hour, the cells were washed three times with PBS for 10 minutes for each wash, and mounted on a coverslip using a Vecta mounting medium (Vector Laboratories, USA) containing 4',6-diamidino-2-phenylindole (DAPI). NIS staining was observed by confocal laser microscopy (Zeiss, LSM 5 exciter, Germany).

9. Establishment of Anaplastic Thyroid Cancer Xenograft Mouse Models

Female Balb/c nude mice, 5.5-week old with an average weight of 18.9±0.37 g (mean±standard deviation [SD]), were purchased (Hamamatsu, Shizuoka, Japan). The mice were acclimated under specific pathogen-free conditions for one week before starting the experiment, and were maintained at a temperature of 20 to 25° C. and a relative humidity of 40 to 70%. To establish anaplastic thyroid cancer xenograft mouse models, 8505C-PNIS-PCMV s ($5 \times 10^6$) were mixed with Matrigel (Corning) at a ratio of 1:1 and injected subcutaneously into the right flank region of each mouse.

10. In Vivo $^{99m}$Tc-Pertechnetate Imaging

When the injected 8505C-PNIS-PCMV cells grew to a size of about 50 mm$^3$, the mice were divided into two groups (n=5): a vehicle group; and a TKI-0266-administered group (50 mg/kg) injected with TKI-0266 by intraperitoneal injection every day for 5 days. To acquire gamma-camera images, 18.5 to 22.2 MBq $^{99m}$Tc-pertechnetate was administered to all the mice by intravenous injection. Whole body pinhole gamma camera imaging using a 2-mm pinhole collimator was acquired by infinia II gamma camera (GE Healthcare, USA). During the experiment, the mice were maintained under anesthesia with isoflurane (Forane, ChoongWae Co., Ltd., Korea). In order to estimate the count value, quantitative analysis was performed by quantifying the regions of interest (hereinafter referred to as ROI) in the mouse tumor region. Finally, in order to confirm the pertechnetate absorbed into the tumor, normalization was performed with a background activity ROI of the same size in the mouse head region.

11. Alalysis by In Vivo Bioluminescence Imaging

In order to examine whether the expression of NIS would be increased by TKI-0266, mice for use in the experiment were divided into two groups (n=5): the vehicle group; and the TKI-0266-administered group (50 mg/kg). 50 mg/kg of TKI-0266 was administered intravenously to the established anaplastic thyroid cancer xenograft mice every day for 5 days. On day 0 (before administration of TKI-0266) and day 6 after the start of administration of TKI-0266, to measure the R-luc signal with IVIS Lumina III, h-coelenterazine (15 μg/ml) was administered to the mice by intravenous injection. Next, D-luciferin (150 μg/ml) was administered intraperitoneally to the mice, and the bioluminescence image (hereinafter referred to as BLI) was acquired.

In addition, in order to evaluate the effect of TKI-0266 administration on the treatment of thyroid cancer, mice for use in the experiment were divided into four groups (n=5): the vehicle group; the $^{131}$I-administered group (injected intraperitoneally with 1 mCi Na-$^{131}$I on day 2 of the experiment; the TKI-0266-administered group (injected intraperitoneally with 50 mg/kg of TKI-0266 for 5 days); and the group co-administered with $^{131}$I and TKI-0266 (injected intraperitoneally with 50 mg/kg of TKI-0266 for 5 days, and injected intravenously with 1 mCi Na-$^{131}$I on day 2; n=5). To measure the degree of tumor growth, h-coelenterazine (15 μg/ml) was administered to the mice by intravenous injection, and then the R-luc activity was monitored by BLI every 5 days.

12. Immunohistochemistry

At the end of the experiment, the mice were sacrificed, and the tumors were isolated from the mouse's right flank and fixed overnight with 4% formalin. The isolated tumors were embedded in paraffin, sectioned to a 4-μm thickness, and mounted on slides. The tumor sections on the slides were de-paraffinized and stained with hematoxylin & eosin. For immunohistochemistry, NIS (Thermo Fisher Scientific; diluted at 1:200) and cleaved caspase-3 (Cell signaling; diluted at 1:200) antibodies were used.

13. Statistical Analysis

All experimental results are expressed as mean±SD. The results from two groups were statistically analyzed by Student's t-test using GraphPad Prism 5 software version 5.01 (GraphPad Software, Inc., USA). A P value of less than 0.05 was considered statistically significant. Error bars represent standard deviations (SD).

Experimental Results

1. Establishment of Anaplastic Thyroid Cancer Cells Containing pNIS-FL2-TurboFP635-pCMV-Rluc Recombinant Vector To monitor the transcriptional regulation of NIS promoter expression in anaplastic thyroid cancer cells, an anaplastic thyroid cancer cell line containing a pNIS-FL2-TurboFP635-pCMV-Rluc recombinant vector (FIG. 1) which is a dual-reporter gene expression system was established. 8505C cells were transfected with the recombinant vector and then analyzed by FACS (fluorescent-activated cell sorting). As a result, it could be seen that 95.2% of the cells were TurboFP365-positive. The TurboFP365-positive cells were named 8505C-PNIS-PCMV cells.

Whether F-luc2, R-luc and TurboFP635 would be expressed in the 8505C-PNIS-PCMV cells was examined to verify whether the reporter genes would be driven. As a result, it could be confirmed that F-luc2, R-luc and TurboFP635 were stably expressed in the 8505C-PNIS-PCMV cells, not 8505C cells.

Figure 2:
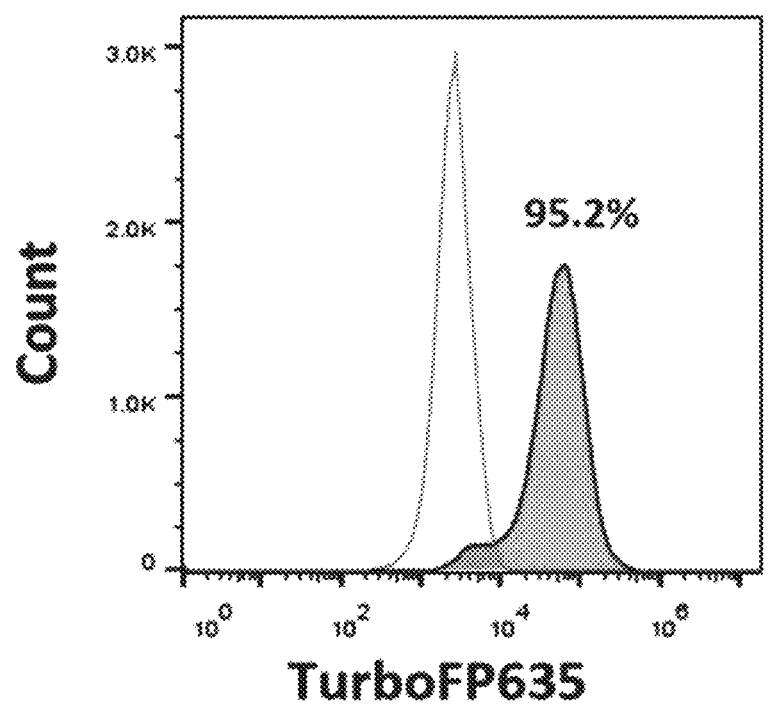
FIG. 2 shows the results of FACS (fluorescent activated cell sorting) analysis performed after transfecting a pNIS-FL2-TurboFP635-pCMV-Rluc vector into 8505C cells.

FIG. 2 is a graph showing the results of FACS analysis performed after transfecting the pNIS-FL2-TurboFP635-pCMV-Rluc vector into 8505C cells.

Figure 3:
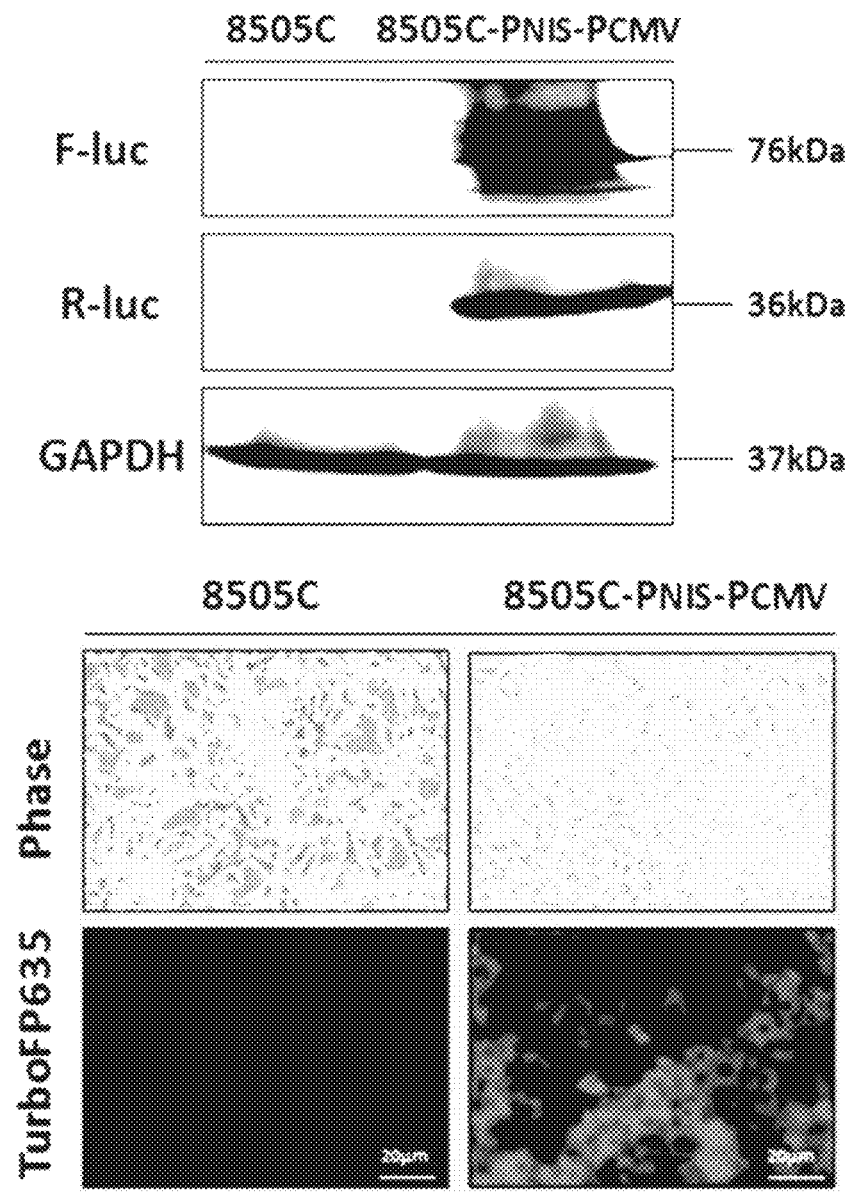
FIG. 3 shows the results of analyzing the expression levels of F-luc2 (firefly luciferase 2), R-luc (Renilla luciferase) and TurboFP635 in 8505C-PNIS-PCMV cells.

FIG. 3 depicts images showing the results of analyzing the expression levels of F-luc2, R-luc and TurboFP635 in the 8505C-PNIS-PCMV cells.

Figure 4:
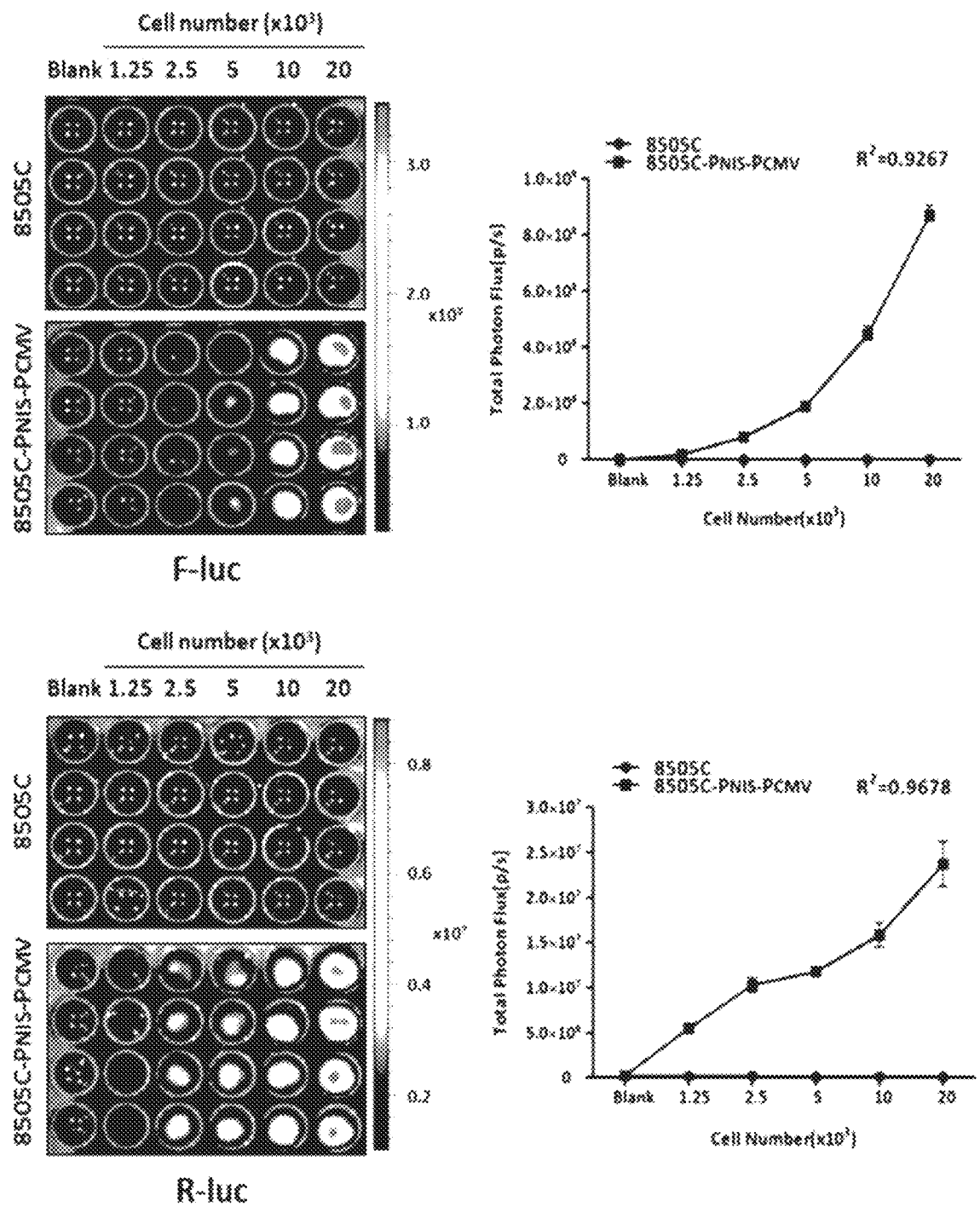
FIG. 4 shows the results of analyzing the expression levels of F-luc2 and R-luc in 8505C-PNIS-PCMV cells by bioluminescence imaging (BLI).

FIG. 4 shows the results of analyzing the expression levels of F-luc2 and R-luc in the 8505C-PNIS-PCMV cells by bioluminescence imaging (hereinafter referred to as BLI). As can be seen therein, as the number of the cells increased, the BLI signal intensity also increased significantly.

2. Screening of Substance that Increases NIS Expression

8505C-PNIS-PCMV cells were treated with TKI candidates for 24 hours, and then the BLI signal was examined, thereby excavating TKI-0266. It could be seen that when the cells were treated with TKI-0266 (hereinafter referred to as the TKI-0266-treated group), the BLI signal activity of F-luc2, which indicated the NIS promoter activity, 3.19-fold increased, and the BLI signal activity of R-luc, which indicates cell viability, was about 75% compared to that in the vehicle group. From the above experimental results, it can be seen that TKI-0266 can regulate the activity of NIS promoter.

Figure 5:
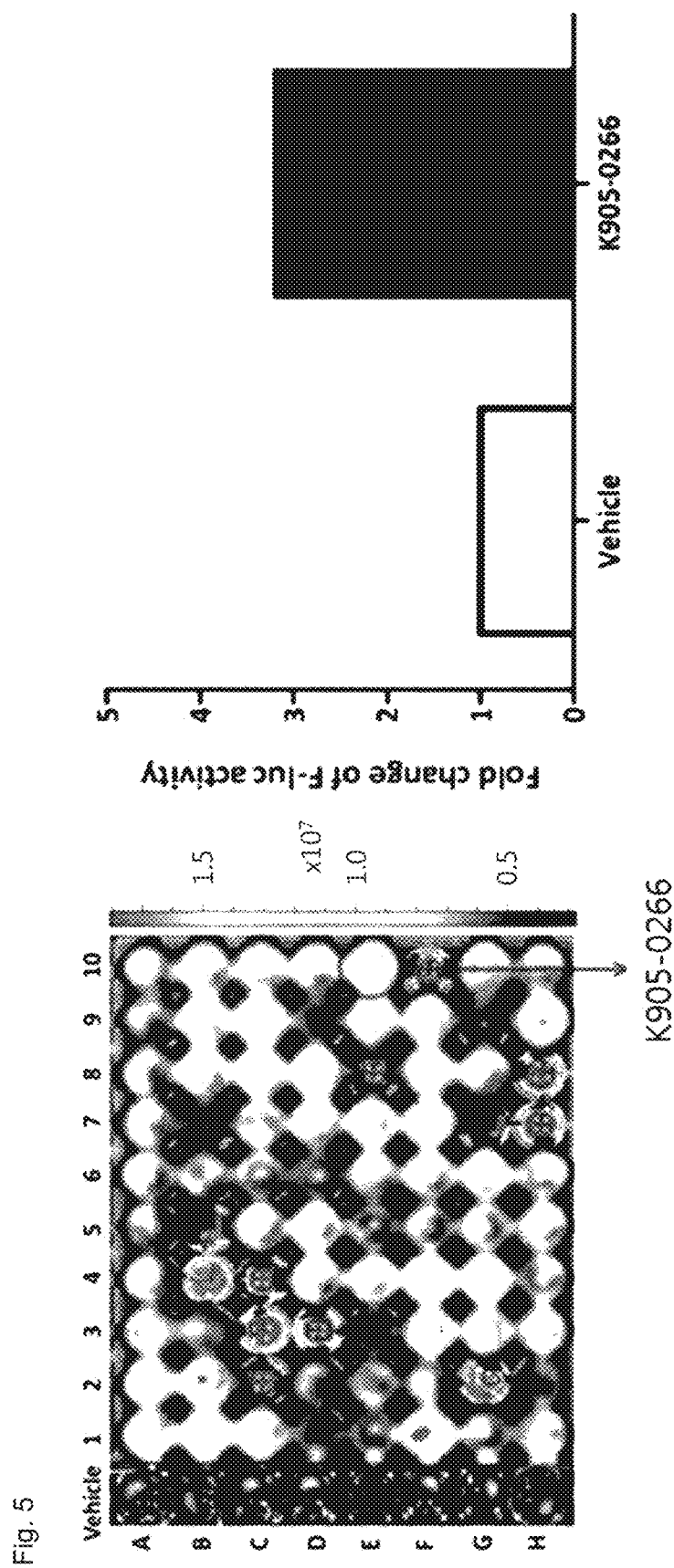
FIG. 5 shows the results of examining the BLI signal for F-luc2 after treating 8505C-PNIS-PCMV cells with a TRI (tyrosine kinase inhibitor) candidate.

FIG. 5 shows the results of analyzing the BLI signal for F-luc2 after treating 8505C-PNIS-PCMV cells with a TKI candidate.

Figure 6:
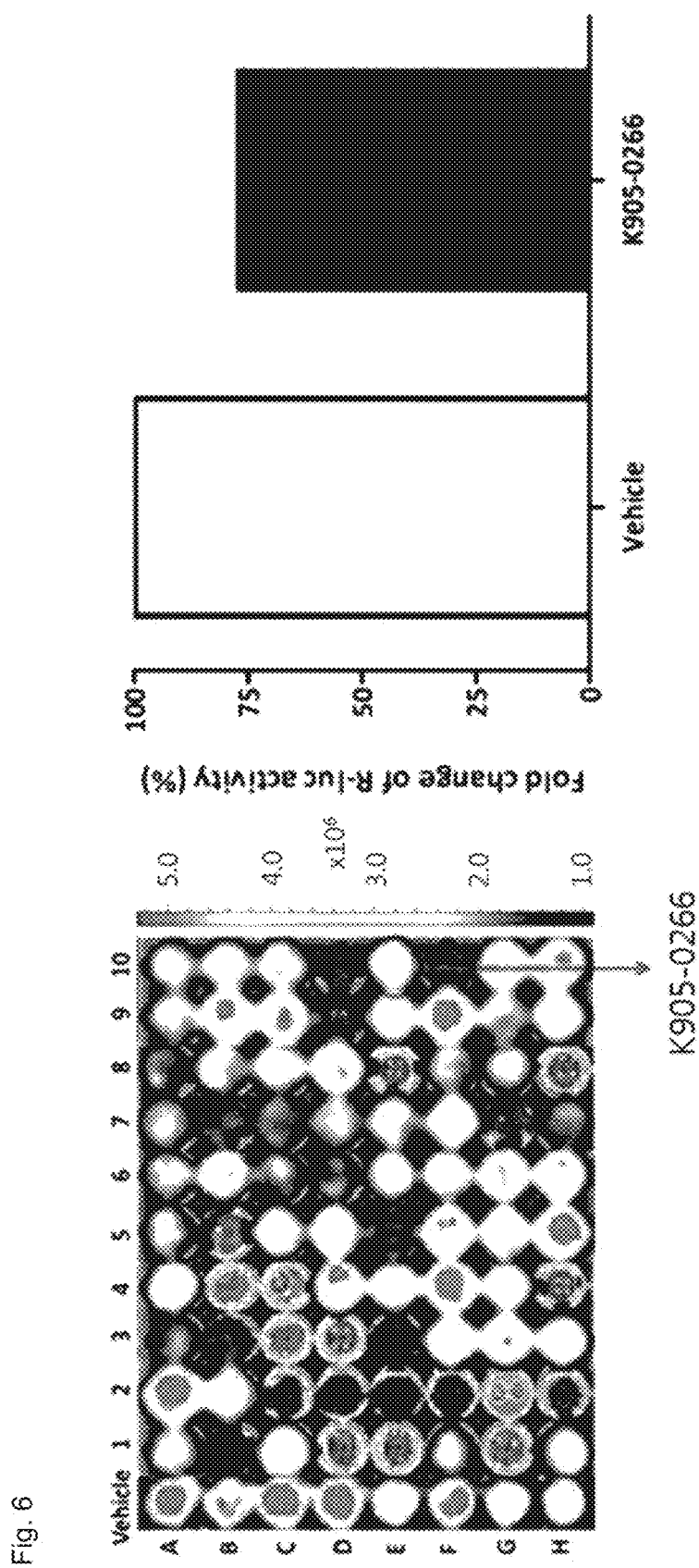
FIG. 6 shows the results of examining the BLI signal for R-luc after treating 8505C-PNIS-PCMV cells with a TKI (tyrosine kinase inhibitor) candidate.

FIG. 6 shows the results of analyzing the BLI signal for R-luc after treating 8505C-PNIS-PCMV cells with a TKI candidate.

3. Confirmation of the Increase in NIS Promoter Activity by TKI-0266

After 8505C-PNIS-PCMV cells were treated with TKI-0266, the activity of NIS promoter was measured depending on the treatment time and the treatment concentration.

As a result, it could be seen that as the treatment concentration of TKI-0266 increased, the BLI signal of F-luc2 increased, and the concentration of 12.5 μM showed the highest activity. On the other hand, it was confirmed that the BLI signal activity of R-luc did not significantly differ between the vehicle group and the TKI-0266-treated group. NIS promoter activity normalized by cell viability means a difference in F-luc2 and R-luc signal intensity.

Figure 7:
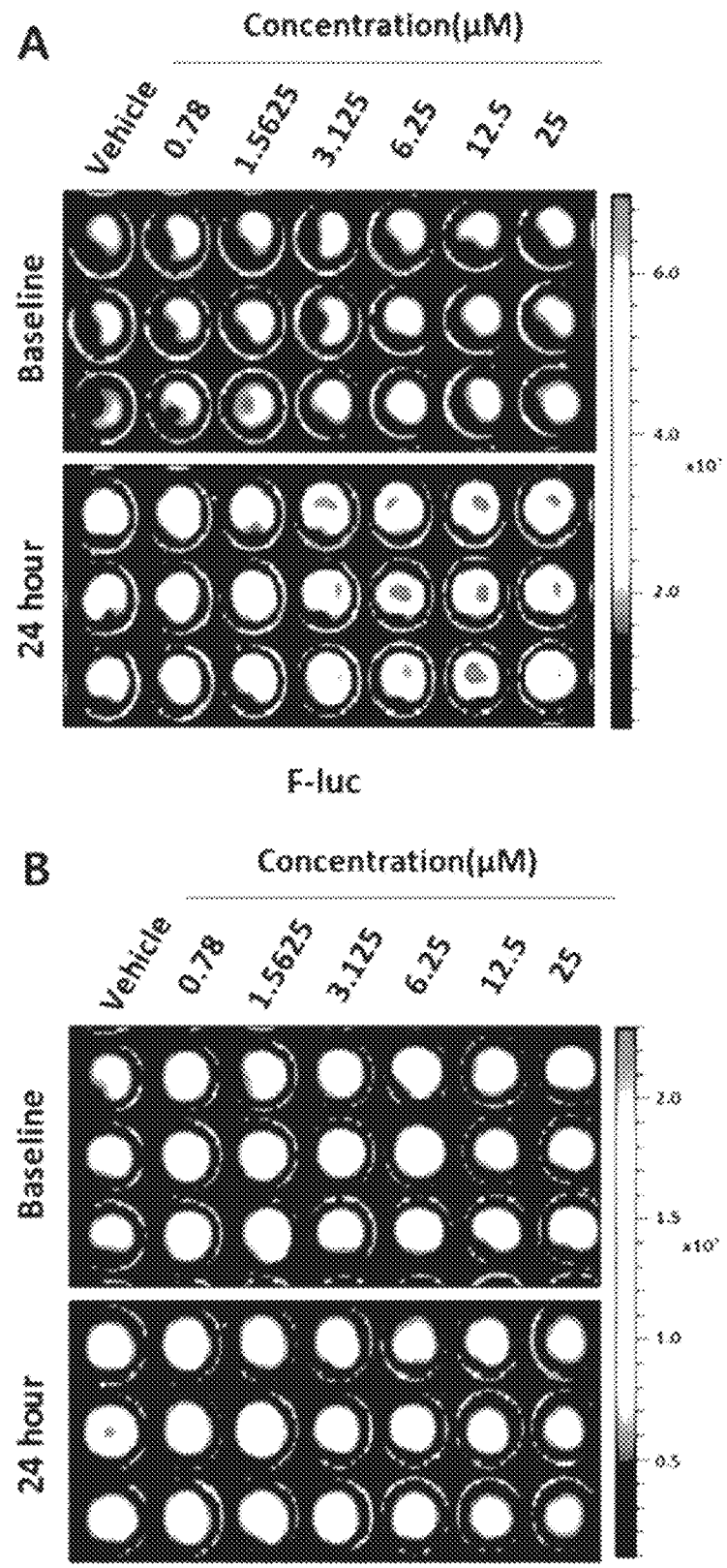
FIG. 7 shows the results of measuring the BLI signal activities of F-luc2 and R-luc in 8505C-PNIS-PCMV cells treated with TKI-0266.

FIG. 7 shows the results of measuring the BLI signal activities of F-luc2 and R-luc after treating 8505C-PNIS-PCMV cells with TKI-0266. Specifically, FIG. 7A shows the results of measuring the BLI signal activity of F-luc2, and FIG. 7B shows the results of measuring the BLI signal activity of R-luc.

Figure 8:
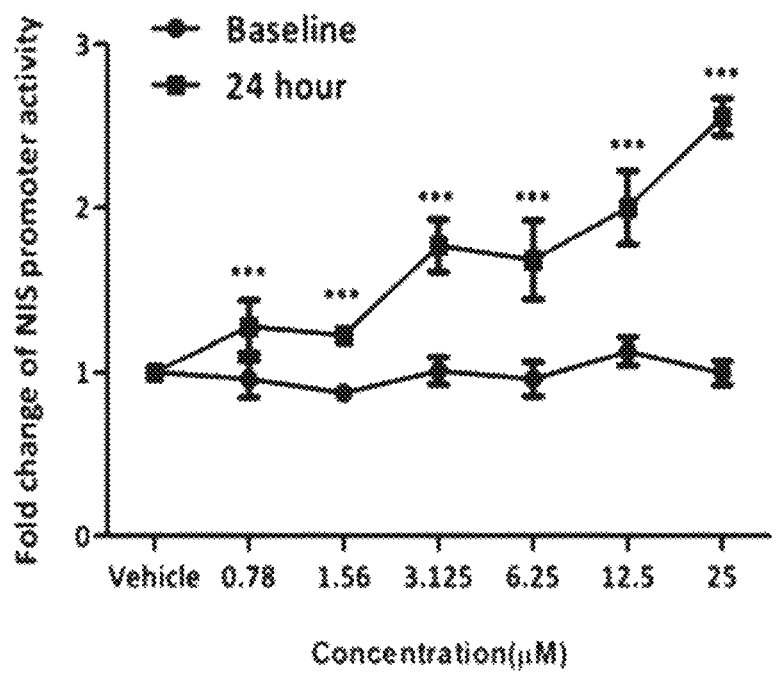
FIG. 8 shows the change in activity of an NIS promoter in 8505C-PNIS-PCMV cells depending on the treatment concentration of TKI-0266.

FIG. 8 shows the change in activity of NIS promoter in 8505C-PNIS-PCMV cells depending on the treatment concentration of TKI-0266. As shown therein, it could be confirmed that as the treatment concentration increased, the activity of NIS promoter also increased.

4. Examination of Change in Protein Expression in 8505C-PNIS-PCMV Cells by TKI-0266

4-1. Examination of Change in NIS Expression

Whether the expression of endogenous NIS protein would be changed by TKI-0266 treatment was examined. As a result, it could be confirmed that the expression of endogenous NIS protein in the TKI-0266-treated group significantly increased, and the expression of NIS protein was the highest when the treatment concentration was 12.5 μM. The quantitative analysis of the band intensity on the Western blot also showed the same results.

In addition, as a result of examining intracellular regions expressing the NIS protein, it could be confirmed that expression of the NIS protein increased mainly in the cell membrane and that the expression of cytosolic NIS protein by TKI-0266 treatment was uptick.

Figure 9:
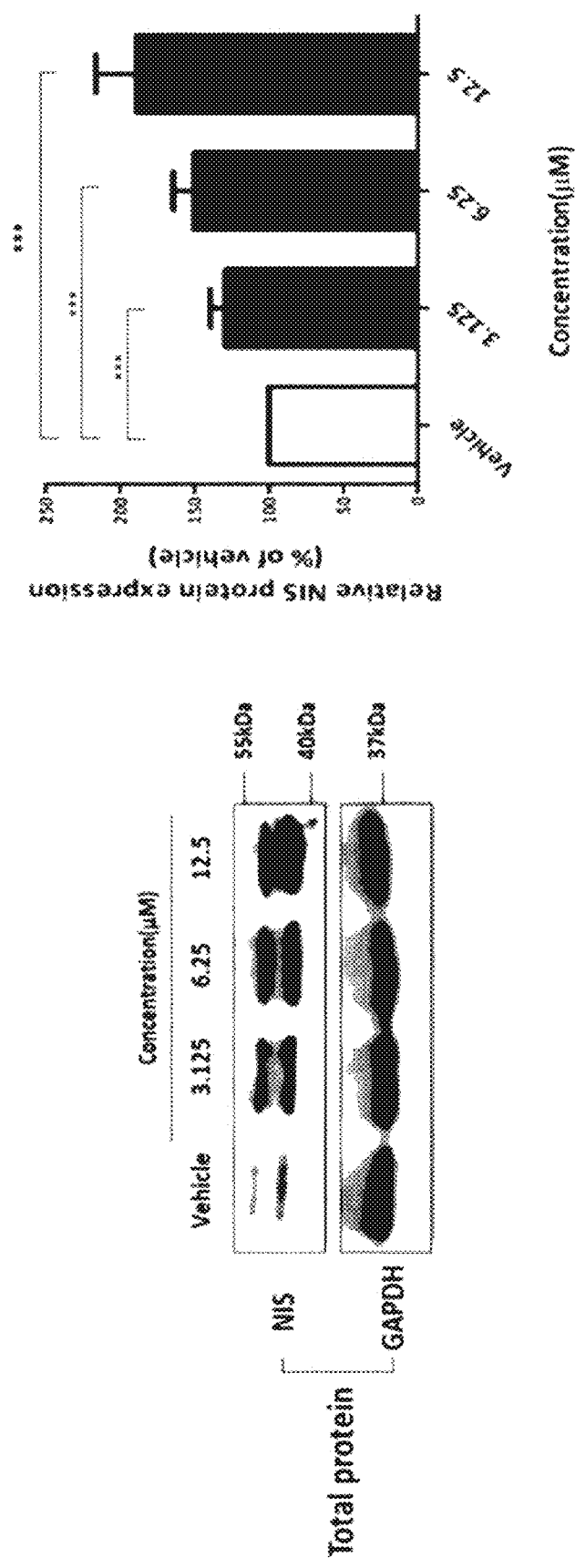
FIG. 9 shows the results of analyzing changes in expression of endogenous NIS protein after treating 8505C-PNIS-PCMV cells with TKI-0266.

FIG. 9 shows the results of examining the change in expression of endogenous NIS protein after treating 8505C-PNIS-PCMV cells with TKI-0266.

Figure 10:
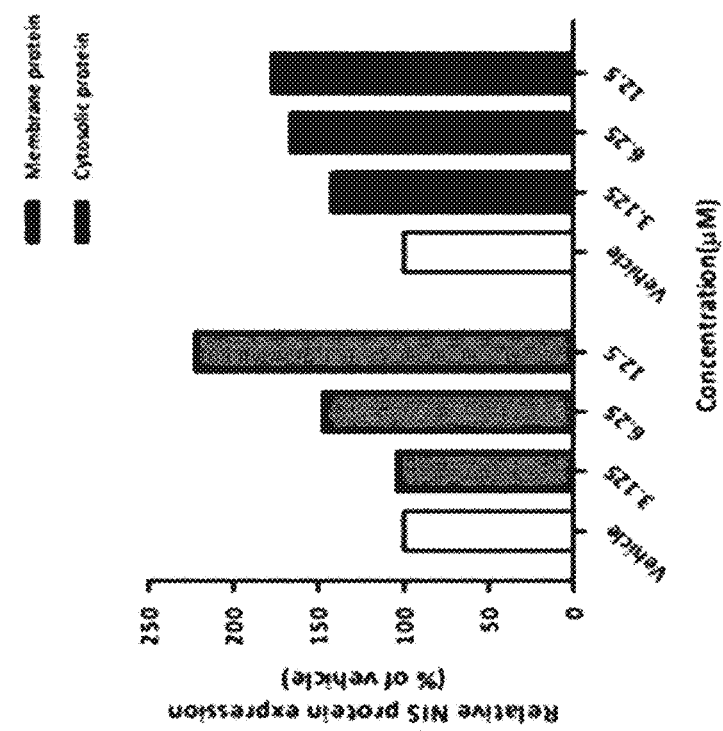
FIG. 10 shows the results of analyzing changes in expression of NIS protein in different cell regions after treating 8505C-PNIS-PCMV cells with TKI-0266.
Figure 10:
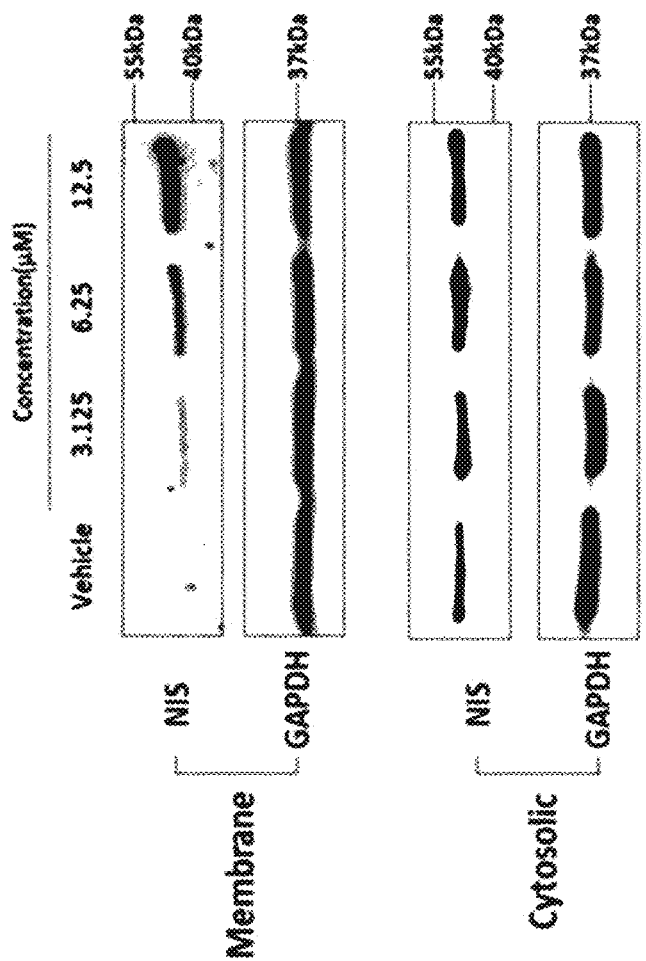

FIG. 10 shows the results of examining the changes in expression of endogenous NIS protein in different cell regions after treating 8505C-PNIS-PCMV cells with TKI-0266.

4-2. Examination of Protein Involved in MAPK Signaling Pathway

The effect of TKI-0266 on the MAPK (mitogen-activated protein kinase) and PI3K-AKT signaling pathway related to the expression of thyroid-specific genes was evaluated.

As a result, it could be seen that the level of phosphorylated-AKT (hereinafter referred to as p-AKT) protein had little difference between the vehicle group and the TKI-0266-treated group. However, it could be confirmed that the level of phosphorylated ERK (hereinafter referred to as p-ERK) protein significantly decreased in the TKI-0266-treated group.

Figure 11:
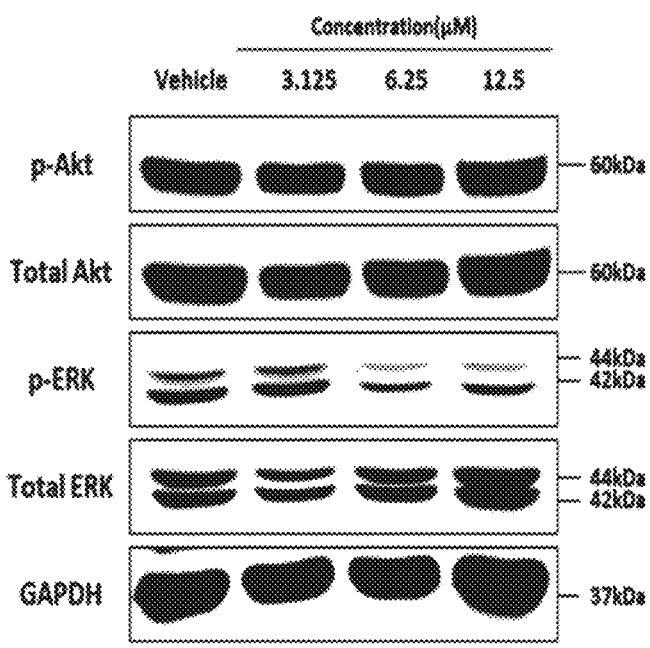
FIG. 11 shows the results of analyzing the protein levels of p-AKT and p-ERK after treating 8505C-PNIS-PCMV cells with TKI-0266.

FIG. 11 shows the results of analyzing the protein levels of p-AKT and p-ERK after treating 8505C-PNIS-PCMV cells with TKI-0266.

4-3. Examination of Changes in Expression of TPO, TSHR, Tg, TTF-1 and Pax-8

TPO (thyroid peroxidase), TSHR (thyroid stimulatine hormone receptor), Tg (thyroglobulin), TTF-1 (thyroid transcription factor-1) and Pax8 (paired box gene 8) are known to play an important role in thyroid follicular cells. Changes in the expression of the proteins in the 8505C-PNIS-PCMV cells were examined, and as a result, it could be confirmed that the expression of the proteins increased in the TKI-0266-treated group.

Figure 12:
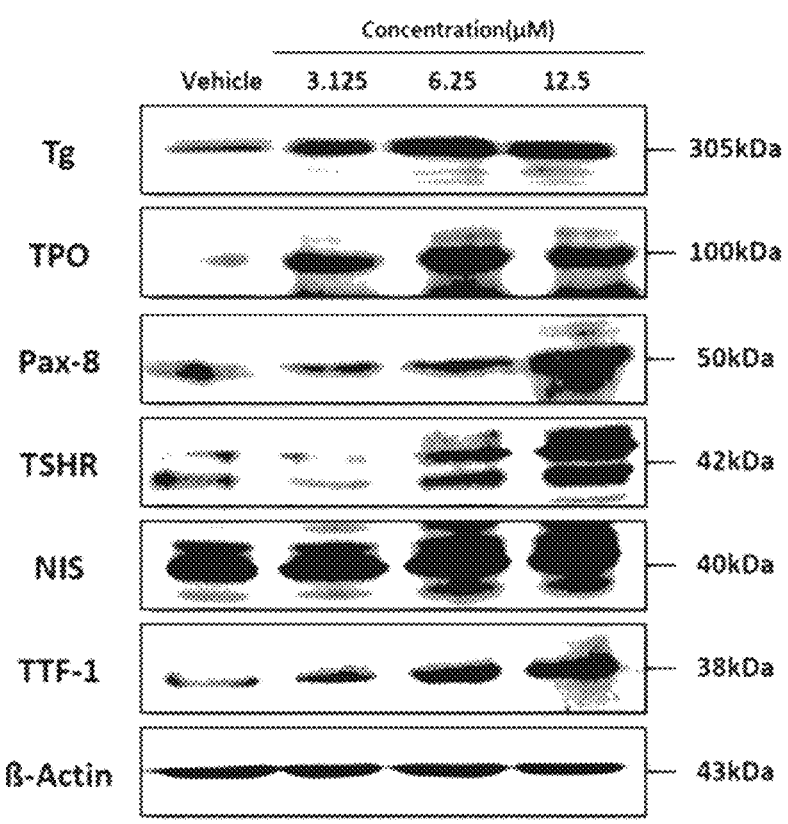
FIG. 12 shows the results of analyzing changes in expression of Tg (thyroglobulin), TPO (thyroid peroxidase), Pax8 (paired box gene 8), TSHR (thyroid stimulatine hormone receptor), NIS (sodium iodide symporter) and TTF-1 (thyroid transcription factor-1) in 8505C-PNIS-PCMV cells depending on the treatment concentration of TKI-0266.

FIG. 12 shows the results of analyzing the changes in expression of Tg, TPO, Pax8, TSHR, NIS and TTF-1 depending on the treatment concentration of TKI-0266. As shown therein, it could be confirmed that as the treatment concentration of TKI-0266 increased, the expression of the proteins also increased.

5. Evaluation of the Effect of TKI-0266 Treatment on Iodine and Radioiodine Uptake in Anaplastic Thyroid Cancer (ATC) Cells Iodine uptake significantly increased in the TKI-0266-treated group compared to the vehicle group, and iodine uptake was completely blocked by treatment with the NIS inhibitor $KClO_4$. In addition, it could be confirmed that the colony-forming ability in the cells in the group co-treated with $^{131}I$ and TKI-0266 significantly decreased compared to that in the vehicle group, the $^{131}I$-treated group and the TKI-0266-treated group. Further, it could be confirmed that the colony-forming ability of the cells in the TKI-0266 treated group decreased compared to that in the vehicle group.

Figure 13:
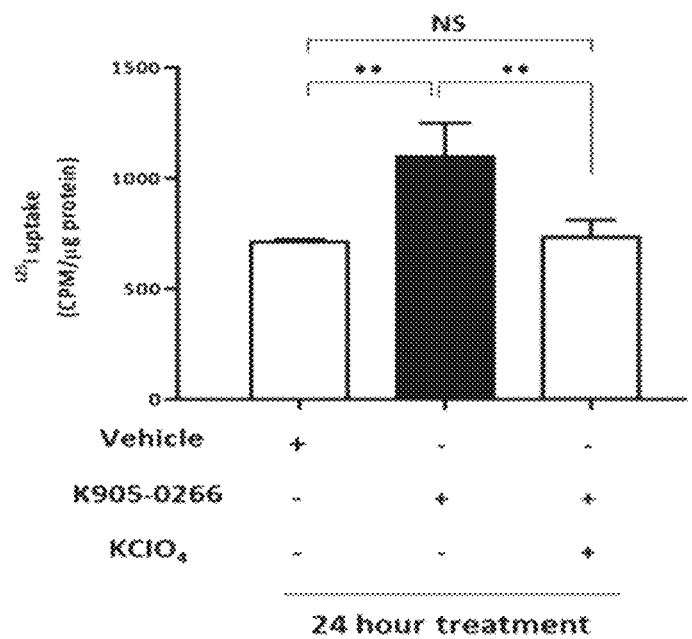
FIG. 13 shows the results of evaluating $^{131}$I uptake depending on whether or not anaplastic thyroid cancer cells were treated with TKI-0266.

FIG. 13 shows the results of evaluating $^{131}I$ uptake in anaplastic thyroid cancer cells depending on whether or not the cells were treated with TKI-0266.

Figure 14:
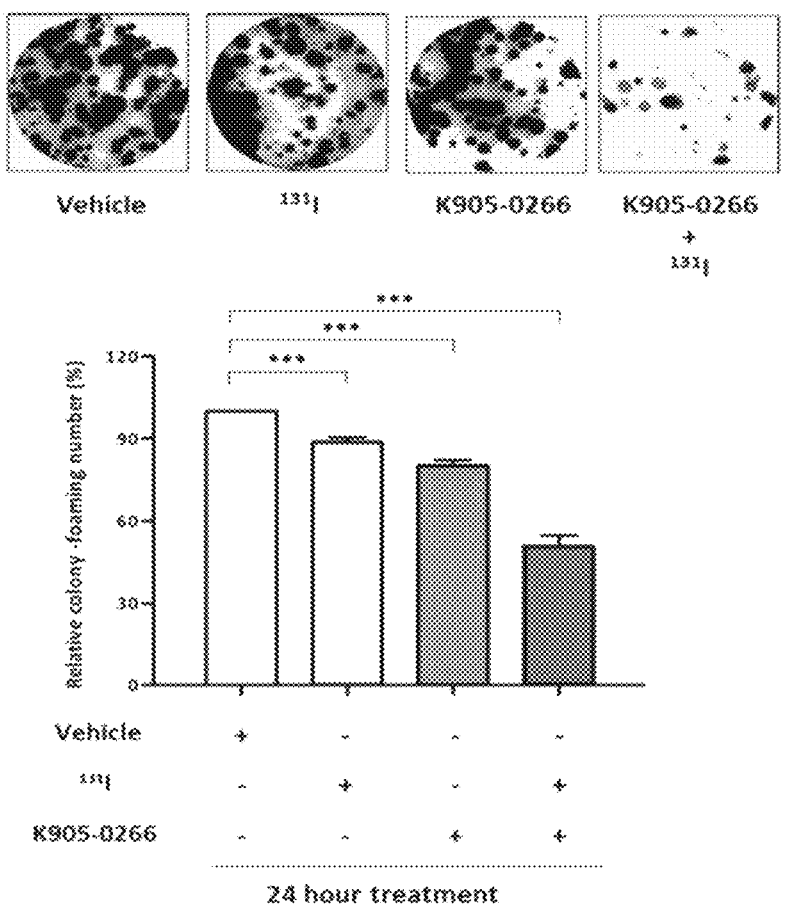
FIG. 14 shows the results of evaluating the colony-forming ability in anaplastic thyroid cancer cells depending on whether or not the cells were treated with TKI-0266.

FIG. 14 shows the results of evaluating the colony-forming ability in anaplastic thyroid cancer cells depending on whether or not the cells were treated with TKI-0266.

6. Examination of Change in NIS Expression in Anaplastic Thyroid Cancer Cells by TKI-0266 Treatment The degree of NIS enhancement by TKI-0266 treatment was examined. As a result, it could be seen that the expression of endogenous NIS expression in the TKI-0266-treated group was robust, but that in the vehicle group was weak.

Figure 15:
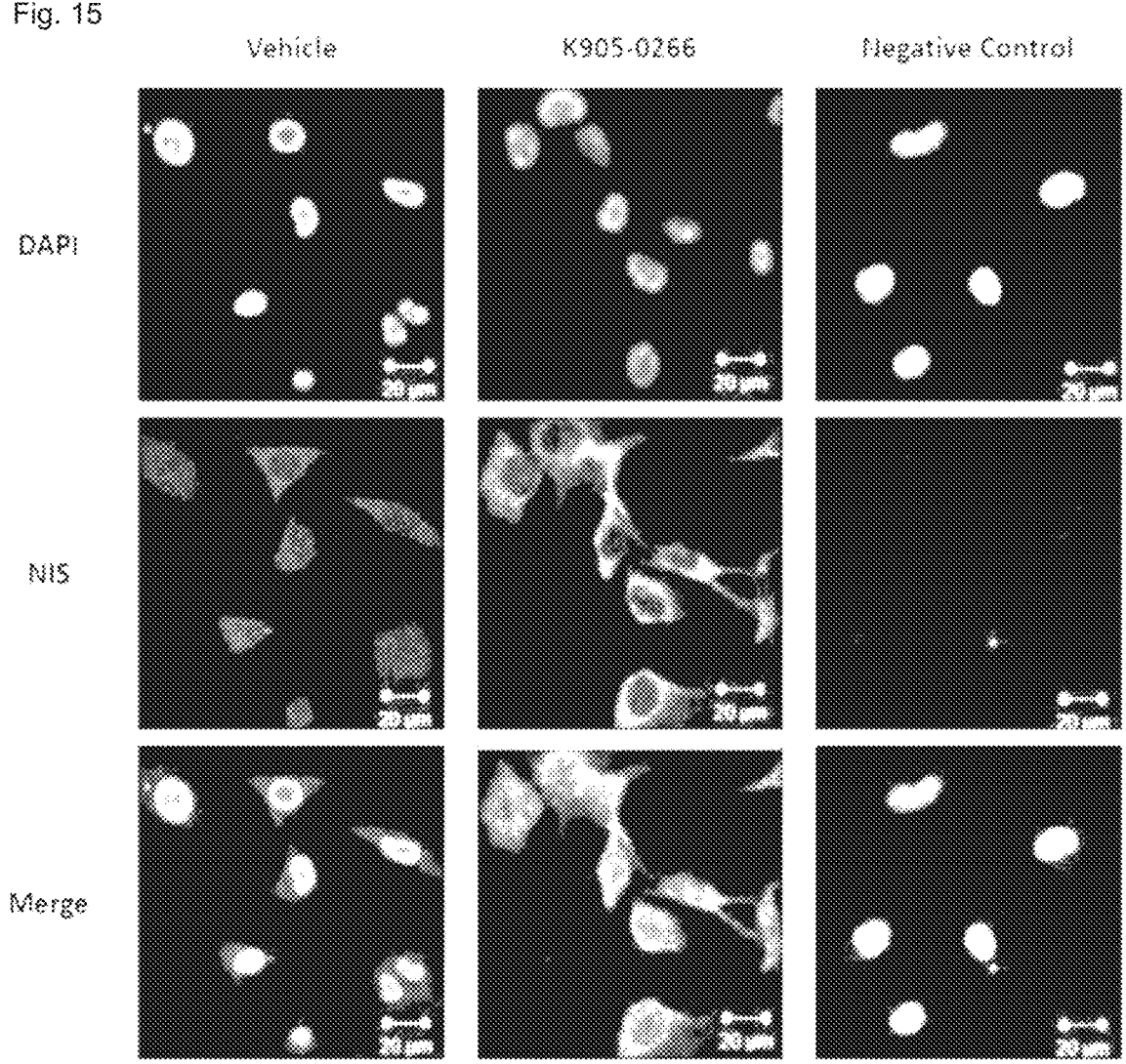
FIG. 15 shows the change in NIS expression in anaplastic thyroid cancer cells by TKI-0266 treatment.

FIG. 15 shows the change in NIS expression in anaplastic thyroid cancer cells by TKI-0266 treatment.

7. Examination of Change in Iodine Uptake in Anaplastic Thyroid Cancer Xenograft Mouse Models by TKI-0266 Administration Based on the in vitro experiment results, whether the increase in NIS expression by TKI-0266 administration would have an effect on the radioisotope uptake in cancer cells was examined.

TKI-0266 was administered to anaplastic thyroid cancer xenograft mice constructed by transplanting 8505C cells ($5\times10^6$), and 18.5 to 22.2 MBq $^{99m}Tc$-pertechnetate was administered to the mice, followed by pinhole gamma camera imaging. As a result, it could be seen that in the case of the TKI-0266-administered group, $^{99m}Tc$-pertechnetate accumulation in the cancer cells significantly increased and the iodine uptake of the thyroid cancer cells was enhanced by TKI-0266 administration.

In particular, it could be confirmed that when 50 mg/kg of TKI-0266 was administered, the radioisotope uptake was the best compared to that in the vehicle group.

Figure 16:
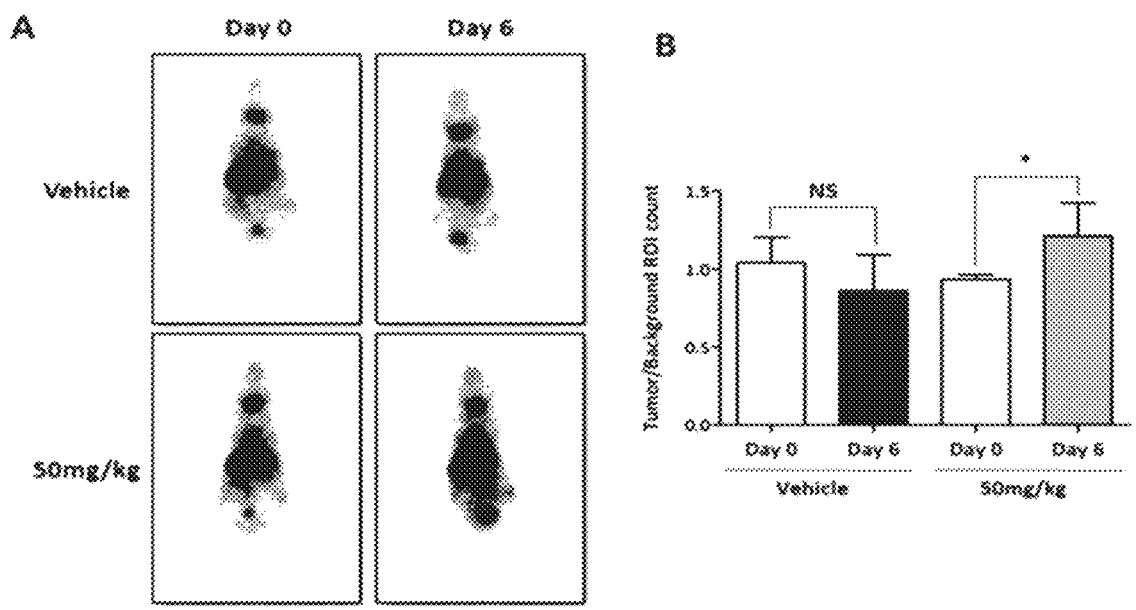
FIG. 16 shows the degree of accumulation of $^{99m}$Tc-pertechnetate following administration of TKI-0266 to anaplastic thyroid cancer xenograft mouse models.

FIG. 16 shows the degree of $^{99m}Tc$-pertechnetate uptake in anaplastic thyroid cancer xenograft mice by TKI-0266 administration. FIG. 16A shows pinhole gamma-camera images, and FIG. 16B graphically shows the results of FIG. 16A. In FIG. 16B, in the case of the vehicle, 1.044±0.148 on day 0, and 0.920±0.047 on day 6, and in the case of the group administered with TKI-0266 (50 mg/kg), 0.852±0.210 on day 0, and 1.21±0.24 on day 6.

8. Examination of Change in Luciferase Activity in Anaplastic Thyroid Cancer Xenograft Mice by TKI-0266 Administration D-luciferin was administered to anaplastic thyroid cancer xenograft mice, and then the activity thereof was monitored. As a result, it could be seen that in the TKI-0266-administered group, the activity of F-luc2 significantly increased, meaning that the expression of NIS increased. In addition, it could be confirmed that in the vehicle group, the activity of F-luc2 was uptick because of tumor growth.

Figure 17:
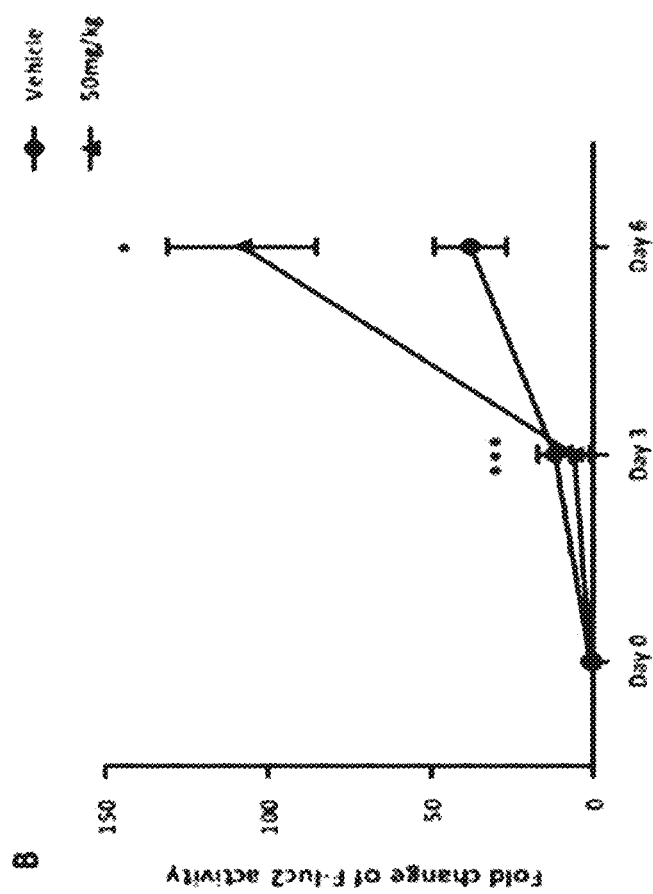
FIG. 17 shows the results of measuring the activity of F-luc2 after administering D-luciferin to undifferentiated thyroid cancer xenograft mouse models.
Figure 17:
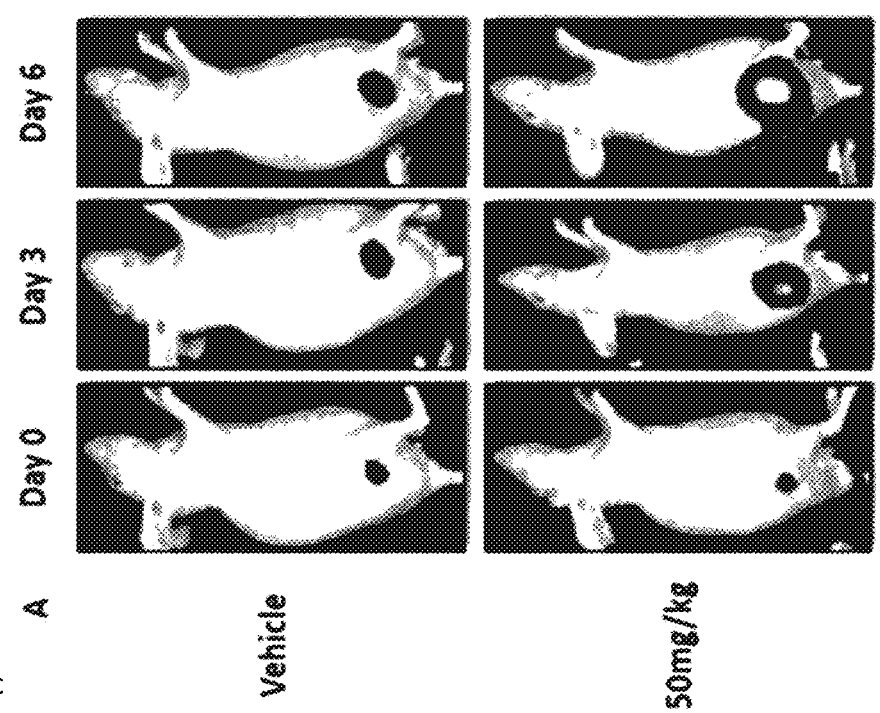

FIG. 17 shows the results of measuring the activity of F-luc2 after administering D-luciferin to anaplastic thyroid cancer xenograft mice.

9. Examination of Tumor Growth Inhibitory Effect of Single Administration of TKI-0266 and Co-Administration of $^{131}I$ and TKI-0266 in Anaplastic Thyroid Cancer Xenograft Mice It could be confirmed that the vehicle group and the group administered with $^{131}I$ alone showed a continuous increase in the tumor size on days 6 and 11, and the group administered with TKI-0266 alone also showed an increase in the Tumor size days 6 and 11. However, it could be confirmed that the group administered with TKI-0266 alone showed a slow tumor growth rate compared to the vehicle group and the group administered with $^{131}I$ alone, indicating that the tumor growth inhibitory effect appeared in the group administered with TKI-0266 alone.

In addition, in the group co-administered with $^{131}I$ and TKI-0266, the R-luc signal intensity decreased on day 6 after administration, and then was restored on day 11 after administration. This suggests that the group co-administered with $^{131}$I and TKI-0266 showed the best tumor growth inhibitory effect among the four experimental groups. However, it could be confirmed that all the experimental groups showed no significant change in the mouse body weight during the experiment.

Figure 18:
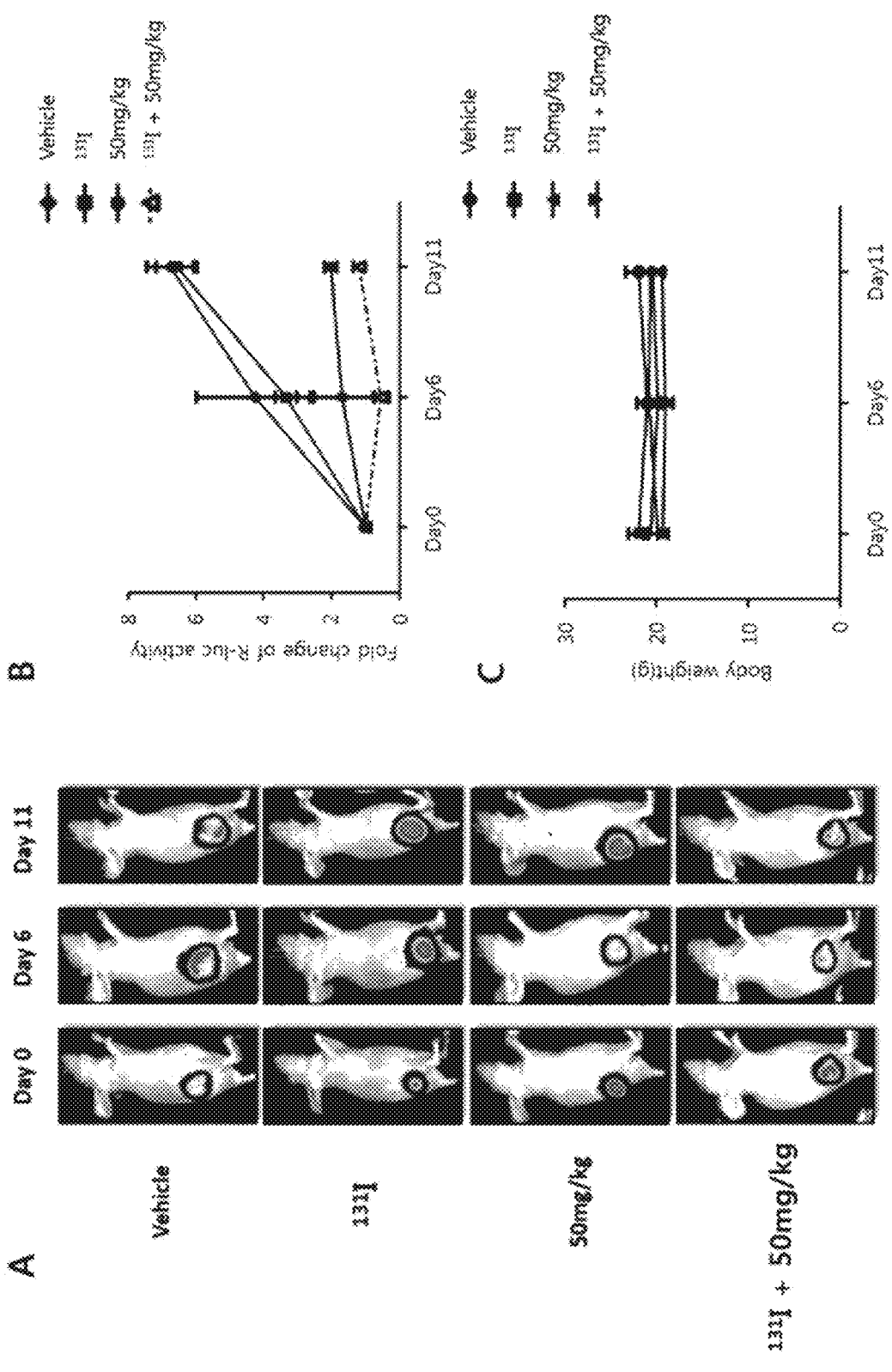
FIG. 18 shows the results of measuring tumor size (A), luciferase activity (B) and body weight (C) after co-administering $^{131}$I and TKI-0266 to undifferentiated thyroid cancer xenograft mouse models.

FIG. 18 shows the results of measuring tumor size (A), luciferase activity (B) and body weight after co-administering $^{131}$I and TKI-0266 to anaplastic thyroid cancer xenograft mice.

10. Confirmation of Increased Expression of NIS and Cleaved Caspase-3 in Anaplastic Thyroid Cancer Xenograft Mice by Administration of TKI-0266 it could be seen that the expression of NIS-specific protein was high in the group administered with TIK-0266, and the expression of cleaved caspase-3 indicating cell death was the highest in the group co-administered with $^{131}$I and TKI-0266.

Figure 19:
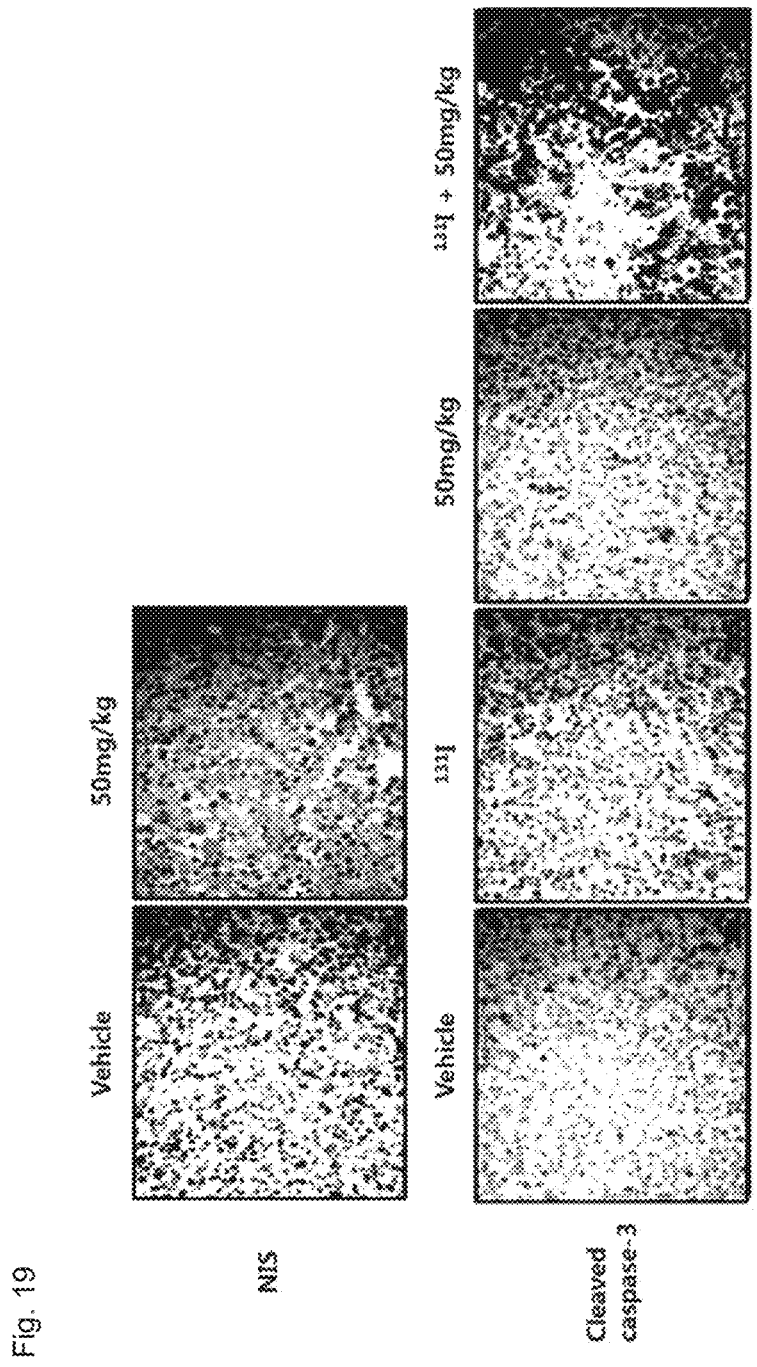
FIG. 19 shows the results of performing immunohistochemistry of NIS and cleaved caspase-3 for tumor tissues sectioned from undifferentiated thyroid cancer xenograft mouse models.

FIG. 19 shows the results of performing immunohistochemistry of NIS and cleaved caspase-3 in tumor tissues sectioned from anaplastic thyroid cancer xenograft mice.

Those skid led in the art to which the present disclosure pertains will appreciate that the present disclosure may be embodied in modified forms without departing from the essential characteristics of the present disclosure. Therefore, the disclosed embodiments should be considered as being illustrative in all respects, rather than restrictive. The scope of the present disclosure should be defined by the appended claims rather than the above description, and all differences within the scope equivalent to the claims should be interpreted as falling within the scope of the present disclosure.

The invention claimed is:

1. A method for treating thyroid cancer comprising administering a compound of the following Formula 1, a salt thereof or a solvate thereof as an active ingredient in a pharmaceutically effective amount to a subject in need thereof:

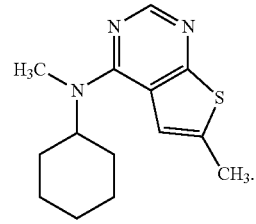

[Formula 1]

2. The method for treating thyroid cancer of claim 1, wherein the thyroid cancer is anaplastic thyroid cancer or differentiated thyroid cancer.

3. The method for treating thyroid cancer of claim 1, wherein the compound of Formula 1 increases expression of sodium iodide symporter.

4. A method for treating thyroid cancer comprising administering anticancer adjuvant containing a compound of the following Formula 1, a salt thereof or a solvate thereof in a pharmaceutically effective amount to a subject in need thereof:

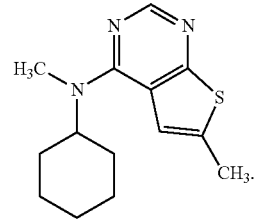

[Formula 1]

5. The method for treating thyroid cancer of claim 4, wherein the compound of Formula 1 increases expression of sodium iodide symporter.

* * * * *